(12) United States Patent
Hecht et al.

(10) Patent No.: US 7,307,735 B2
(45) Date of Patent: Dec. 11, 2007

(54) METHOD FOR DETERMINING THE DEPTH OF A BURIED STRUCTURE

(75) Inventors: Thomas Hecht, Dresden (DE); Uwe Schröder, Dresden (DE); Ulrich Mantz, Dresden (DE); Stefan Jakschik, Dresden (DE); Andreas Orth, Dresden (DE)

(73) Assignee: Infineon Technologies AG, Munich (DE)

( * ) Notice: Subject to any disclaimer, the term of this patent is extended or adjusted under 35 U.S.C. 154(b) by 181 days.

(21) Appl. No.: 10/835,259

(22) Filed: Apr. 30, 2004

(65) Prior Publication Data

US 2005/0003642 A1     Jan. 6, 2005

(30) Foreign Application Priority Data

May 3, 2003     (DE) ................... 103 19 843

(51) Int. Cl.
*G01B 11/02* (2006.01)
(52) U.S. Cl. ............................ 356/504
(58) Field of Classification Search ............ 356/492, 356/493, 503, 504
See application file for complete search history.

(56) References Cited

U.S. PATENT DOCUMENTS

| | | | | |
|---|---|---|---|---|
| 5,034,617 A | * | 7/1991 | Isobe | ............ 250/559.28 |
| 5,227,861 A | * | 7/1993 | Nishizawa et al. | ......... 356/497 |
| 5,371,596 A | * | 12/1994 | Hattori et al. | ............. 356/497 |
| 5,384,639 A | * | 1/1995 | Wickramasinghe | ......... 356/496 |
| 5,392,118 A | | 2/1995 | Wickramasinghe | |
| 5,494,697 A | | 2/1996 | Blayo et al. | |
| 5,595,916 A | | 1/1997 | Fujimura et al. | |
| 5,604,581 A | | 2/1997 | Liu et al. | |
| 5,900,633 A | | 5/1999 | Solomon et al. | |
| 6,137,575 A | * | 10/2000 | Sugiyama et al. | ........ 356/503 |
| 6,392,756 B1 | * | 5/2002 | Li et al. | ................. 356/632 |
| 6,950,186 B2 | | 9/2005 | Kikuchi | |

FOREIGN PATENT DOCUMENTS

| | | |
|---|---|---|
| DE | 690 33111 T2 | 9/1990 |
| EP | 0 650030 A2 | 9/1990 |
| JP | 2003-243467 | 8/2003 |
| JP | 2003243467 | 8/2003 |

* cited by examiner

*Primary Examiner*—Michael A. Lyons
(74) *Attorney, Agent, or Firm*—Patterson & Sheridan, L.L.P.

(57) ABSTRACT

The present invention relates to a method for determining the depth of a buried structure in a semiconductor wafer. According to the invention, the layer behavior of the semiconductor wafer which is brought about by the buried structure when the semiconductor wafer is irradiated with electromagnetic radiation in the infrared range and arises as a result of the significantly longer wavelengths of the radiation used in comparison with the lateral dimensions of the buried structure is utilized to determine the depth of the buried structure by spectrometric and/or ellipsometric methods.

15 Claims, 7 Drawing Sheets

METHOD FOR DETERMINING THE DEPTH OF A BURIED STRUCTURE

CLAIM FOR PRIORITY

This application claims the benefit of priority to German Application No. 103 19 843.1, filed in the German language on May 3, 2003, the contents of which are hereby incorporated by reference.

TECHNICAL FIELD OF THE INVENTION

The present invention relates to a plurality of methods for determining the depth of a buried structure in a semiconductor wafer.

BACKGROUND OF THE INVENTION

Electronics is dominated nowadays by microelectronic components with integrated circuits. Such integrated circuits comprise a complex arrangement of electronic structures which are interconnected in a plurality of planes arranged one above the other on a common semiconductor substrate, also referred to as chip. The fabrication of these circuits is characterized by a complicated succession of different process steps.

One of the principle requirements of the semiconductor industry is the continuous increase in performance as a result of ever faster circuits, which is linked with the miniaturization of the electronic structures. In the course of this development, a transition has been made to arranging the structures during the production of the chips on a semiconductor wafer in part for example in etching trenches etched into the semiconductor wafer, so that, as buried structures, they take up less space on the surface of the semiconductor wafer.

The miniaturization of the electronic structures is accompanied by an increase in the requirements made of the precision of the fabrication processes used. At the same time, precise measurement methods are relied on in order to determine the exact position and also the precise geometrical extent of the structures. In this case, the determination of the depth of buried structures, in particular, is accorded great importance since this parameter may have a significant influence on the functionality of the circuits.

In order to determine the depth of a buried structure, it is known to break the semiconductor wafer in the region of said structure and to examine the break edge with the aid of a scanning electron microscope. The image of the break edge that is recorded thereby can be used to determine the depth of the buried structure.

However, this method turns out to be complicated and laborious due to the required breaking of the semiconductor wafer. Furthermore, the semiconductor wafer is destroyed by being broken, as a result of which the method is extremely cost-intensive. Furthermore, since the method cannot be applied to the product wafers which continue in production, deviations may occur between the measured depth of a structure and the depth of a corresponding structure of a product wafer.

As an alternative, in order to determine the depth of a buried structure, it is indeed known to estimate the depth indirectly by way of the etching rates determined during the etching of comparable structures into planar test wafers. It is also correspondingly the case with this method that it does not measure the depths of structures at the product wafers, so that the estimated values may deviate from the depths of the structures in product wafers.

SUMMARY OF THE INVENTION

The present invention provides a nondestructive, cost-effective and fast method for determining the depth of a buried structure in a semiconductor wafer.

In accordance with one embodiment according to the invention, there is a method for determining the depth of a buried structure in a semiconductor wafer, the semiconductor wafer is irradiated at a predetermined angle of incidence with respect to a surface of the semiconductor wafer with electromagnetic radiation in a wavelength range, the wavelengths used lying in the infrared range. The intensity of the reflected radiation is then recorded depending on the wave number of the wavelength range of the radiated-in electromagnetic radiation at an angle of reflection—corresponding to the angle of incidence—with respect to the surface of the semiconductor wafer. Afterward, the depth of the buried structure is determined from the recorded intensity profile, which includes information about constructive and destructive interferences of radiation reflected at the surface of the semiconductor wafer and at the buried structure and, consequently, an item of structural depth information of the semiconductor wafer.

This method enables nondestructive determination of the depth of a buried structure in a semiconductor wafer, so that costs and also time can be saved. At the same time, the method can be applied to a product wafer and can be carried out directly after a process for fabricating the buried structure.

The depth of the buried structure is preferably determined by means of a frequency analysis of the intensity profile, in which, from the information about constructive and destructive interferences which is contained in the intensity profile, it is possible to deduce the optical path differences between the radiation reflected at the surface of the semiconductor wafer and at the buried structure, and thus the depth of the buried structure.

As an alternative, the depth of the buried structure may be determined by comparing the measured intensity profile with an intensity profile calculated on the basis of a model. Optical material parameters of the semiconductor wafer such as refractive indices, for instance, are incorporated into the model.

In order to increase the accuracy of the determination of the depth of the buried structure, the semiconductor wafer is preferably irradiated with electromagnetic radiation with different polarizations. The respective state of polarization of the measured intensity profile, the state of polarization being altered by the reflection, is taken into account as an additional parameter in the model.

In another embodiment according to the invention, there is a method for determining the depth of a buried structure in a semiconductor wafer, it is proposed, to irradiate the semiconductor wafer at different angles of incidence with respect to a surface of the semiconductor wafer with electromagnetic radiation having a predetermined wavelength which lies in the infrared range. The intensity of the reflected radiation is then recorded at an angle of reflection—corresponding to the respective angle of incidence—with respect to the surface of the semiconductor wafer. Afterward, the depth of the buried structure can be determined from the recorded intensity profile, which once again includes information about constructive and destructive interferences of radiation reflected at the surface of the semiconductor wafer and at the buried structure, and thus an item of structural depth information of the semiconductor wafer. This nondestructive method correspondingly has the advantages designated with the first method according to the invention.

Preferably, the depth of the buried structure is determined by an angle of reflection specific Fourier analysis of the intensity profile. In this case, from the information about constructive and destructive interferences which is included in the intensity profile, the optical path differences between the radiation reflected at the surface of the semiconductor wafer and at the buried structure and thus the depth of the buried structure are deduced.

The depth of the buried structure may also optionally be determined by comparing the measured intensity profile with an intensity profile calculated on the basis of a model. Preferably, the semiconductor wafer is in this case irradiated with electromagnetic radiation with different polarizations and the respective state of polarization of the measured intensity profile is additionally taken into account in the model.

In still another embodiment of the invention, there is a method in which the semiconductor wafer is irradiated at a predetermined angle of incidence with respect to a surface of the semiconductor wafer with electromagnetic radiation having a defined polarization, the electromagnetic radiation having a wavelength in the infrared range. The state of polarization of the electromagnetic radiation reflected at the semiconductor wafer is then determined at an angle of reflection—corresponding to the angle of incidence—with respect to the surface of the semiconductor wafer. The superposition of the radiation reflected at the surface of the semiconductor wafer and at the buried structure results in a change in the state of polarization, which change is compared, with a change—calculated on the basis of a model—in the state of polarization with the depth of the buried structure in order to determine the depth of the buried structure. This nondestructive method is also distinguished by the advantages described in connection with the first method according to the invention.

In order to carry out this method, a customary ellipsometer is preferably used, by means of which changes in the state of polarization of radiation reflected at a sample can be determined simply and without any problems.

The invention uses electromagnetic radiation having wavelengths in the infrared range for irradiating the semiconductor wafer. With the aid of this radiation, in contrast to radiation having wavelengths in the optically visible range, it is possible to determine the depth of a structure in the region of a number of μm, since this radiation is distinguished by low absorption and thus a high penetration depth in the semiconductor wafers, essentially composed of silicon. Moreover, the radiation used suppresses scattering effects at the buried structure and thus lateral details which can adversely influence the determination of the depth, since the wavelengths of the radiation, lying approximately in the range of 2 to 20 μm, are significantly greater than the lateral dimensions of the buried structure, which are to be established approximately in the region of 100 nm. As a result of this, the semiconductor wafer, on account of a material change brought about by the buried structure, acts as an apparently homogeneous layer system with different refractive indices at which reflection takes place.

In order to utilize this layer behavior even better, the method or the methods is or are preferably designed for determining the depth of a structure in a semiconductor wafer, the structure having a regular pattern, and the semiconductor wafer being irradiated over a large area in order to achieve a spatial averaging of reflections at a multiplicity of structure elements of the regular pattern.

The above methods are also suitable for determining the depth of structures extending geometrically within the semiconductor wafer, hidden structures or else desired inclusion volumes, provided that reflections take place at these structures.

According to the invention, the methods proposed utilize the approximately homogeneous layer behavior of the semiconductor wafer and of the buried structure which is brought about by the electromagnetic radiation in the infrared range.

BRIEF DESCRIPTION OF THE DRAWINGS

The invention is explained in more detail below with reference to the figures, in which.

DETAILED DESCRIPTION OF THE INVENTION

Figure 1:
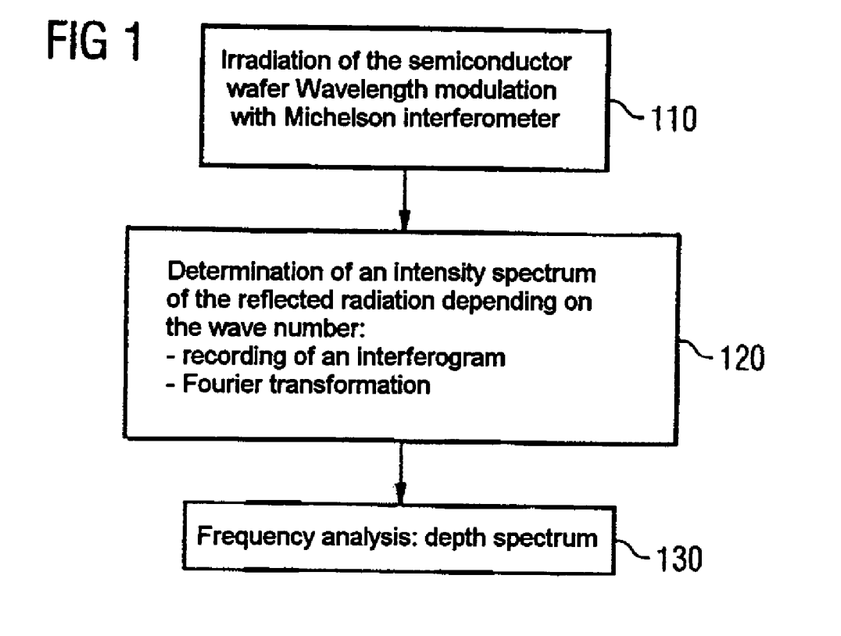
FIG. 1 shows a flow diagram of a first embodiment of a method according to the invention.

FIG. 1 shows a flow diagram of a first embodiment of a method according to the invention for determining the depth of a buried structure in a semiconductor wafer. For this purpose, in 110, the semiconductor wafer is irradiated at a predetermined angle of incidence with respect to a surface of the semiconductor wafer with electromagnetic radiation in a wavelength range, the wavelengths used lying in the infrared range and being modulated in a frequency-dependent manner with the aid of a Michelson interferometer. In this case, the modulation of the wavelengths is dependent on the position of a movable mirror of the Michelson interferometer.

In 120, an intensity spectrum of the reflected radiation is determined depending on the wave number of the wavelength range of the radiated-in electromagnetic radiation at an angle of reflection—corresponding to the angle of incidence—with respect to the surface of the semiconductor wafer. Stepp 120 can be split into two substeps. In a first substep, the intensity of the reflected radiation is recorded depending on the position of the movable mirror, a so-called interferogram. From this interferogram, by means of a Fourier transformation, it is possible subsequently to calculate the intensity spectrum of the reflected radiation depending on the wave number. The intensity spectrum thus obtained includes in particular information about constructive and destructive interferences of radiation reflected at the surface of the semiconductor wafer and at the buried structure.

A frequency analysis of the intensity spectrum, which is carried out in 130 and in which the optical path differences between the radiation reflected at the surface of the semiconductor wafer and at the buried structure can be deduced from the information about constructive and destructive interferences which is contained in the intensity spectrum, is used to obtain a depth structure of the semiconductor wafer or a depth spectrum—referred to below—of the buried structure within the semiconductor wafer.

This method for determining the depth of a buried structure in a semiconductor wafer is explained in more detail with reference to FIGS. 2 to 5 hereinafter.

Figure 2:
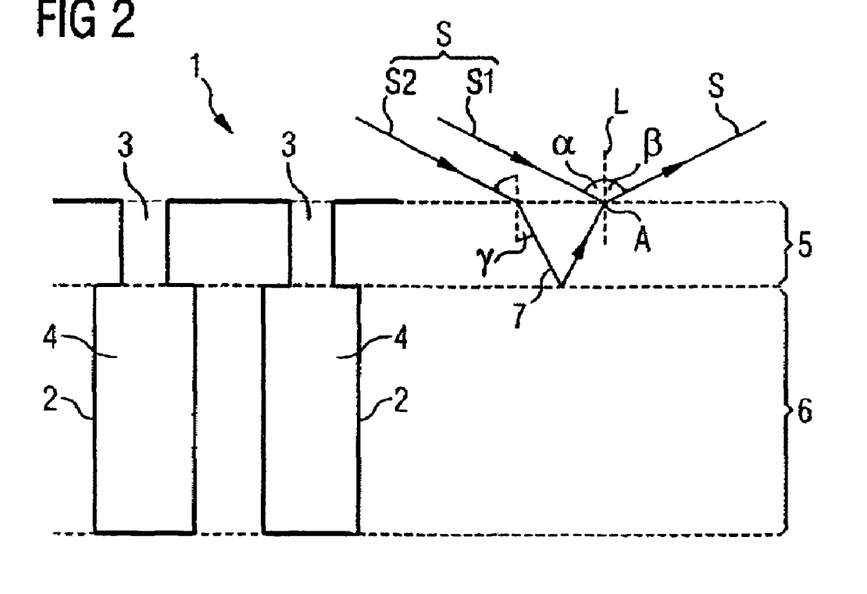
FIG. 2 shows a diagrammatic sectional illustration of a top side of a semiconductor wafer having trench structures with interfering electromagnetic partial beams.

FIG. 2 shows a diagrammatic sectional illustration of a top side of a semiconductor wafer 1, which has trench structures 2 for trench capacitors as an example of a buried structure. These trench capacitors, which are employed on DRAM memory chips, are arranged during fabrication in etching trenches of the semiconductor wafer 1, said etching trenches being formed as trench structures 2, in order to optimally utilize the surface of the later DRAM memory chip. In the course of continuously advancing miniaturization of the surface structures, the trench structure 2 is laterally expanded in the lower region by additional etching processes in order that the surface area available for the capacitor and thus the capacitance are kept approximately constant despite miniaturization of the surface structures. The trench structure 2 can therefore be divided into a thin upper trench section 3 and a wider lower trench section 4.

Since, in particular, the depth of the upper trench section 3 has a significant influence on the functionality of the later DRAM memory chip, it is endeavored to determine this depth after a process for fabricating the trench structure 2. The method for determining the depth of a buried structure in a semiconductor wafer as illustrated in FIG. 1 is especially suitable for this because it manages without destroying the semiconductor wafer.

The electromagnetic radiation used having wavelengths in the infrared range proves to be highly favorable for determining a depth spectrum of the trench structure 2 illustrated, which extends over a depth range of a number of μm. In contrast to radiation having wavelengths in the optically visible range, the radiation used is distinguished by a low absorption and thus a high penetration depth in the semiconductor wafer 1, essentially composed of silicon. Moreover, the radiation used suppresses scattering effects at the trench structure 2 and consequently lateral details of the trench structure 2 which may adversely influence the determination of the depth, because the wavelengths of the radiation of approximately 2 to 20 μm are significantly greater than the lateral dimensions of the trench structure 2 in the region of 100 nm. On account of the fact that on average a different ratio of silicon and air prevails in the region of the upper trench section 3 than in the region of the lower trench section 4, these regions therefore act as different, apparently homogeneous layers with regard to optical properties. These layers are referred to below as upper layer 5 and lower layer 6, respectively.

If, as illustrated further in FIG. 2, electromagnetic radiation S of one wavelength impinges on the surface of the semiconductor wafer 1 at an angle α of incidence with respect to a perpendicular L, then one part of the radiation, illustrated by a partial beam S1, is reflected at an angle β of reflection—corresponding to the angle a of incidence—on the surface of the semiconductor wafer 1. Another part of the radiation, illustrated by a partial beam S2, penetrates into the surface of the semiconductor wafer 1 and thus into the upper layer 5 and is refracted at an angle γ of refraction with respect to the perpendicular. Since the upper layer 5 and the lower layer 6 differ with regard to their material composition or average density, at the interface between upper layer 5 and lower layer 6 there is a gradient in the refractive index, which leads to a reflection of the partial beam S2 at the interface. The partial beam S2 impinges on the surface of the semiconductor wafer 1 again at the point A and is refracted away from the perpendicular L at the angle β of reflection.

A superposition and thus an interference of the two partial beams S1 and S2 occurs at the point A. Compared with the partial beam S1 reflected at the surface of the semiconductor wafer 1, the partial beam S2 reflected at the interface between upper layer 5 and lower layer 6 has traversed an optical path difference 7.

If electromagnetic radiation of a different wavelength is now considered, then a different angle of refraction and thus a different optical path difference result on account of the dispersion. Electromagnetic radiation of one wavelength range accordingly leads to different optical path differences which influence the intensity profile measured in reflection depending on the wave number or wavelength. In a converse conclusion, therefore, by determining the intensity profile, it is possible to determine the optical path differences at the different wavelengths of a wavelength range and thus the thickness of the upper layer 5, which corresponds to the depth of the upper trench section 3.

It becomes clear from this mode of consideration that the one embodiment of a method according to the invention as illustrated in FIG. 1 is suitable for determining the depth of a buried structure all the more reliably, the better the structure behaves as a homogeneous layer system upon irradiation with electromagnetic radiation in the infrared range. Therefore, the method is preferably designed for determining the depth of a structure having a regular pattern in a semiconductor wafer, the semiconductor wafer being irradiated in a large-area manner in order to obtain a spatial averaging of reflections at a multiplicity of structure elements of the regular pattern. This applies analogously to the further embodiments of a method according to the invention as described with reference to FIGS. 6 to 11.

Figure 3:
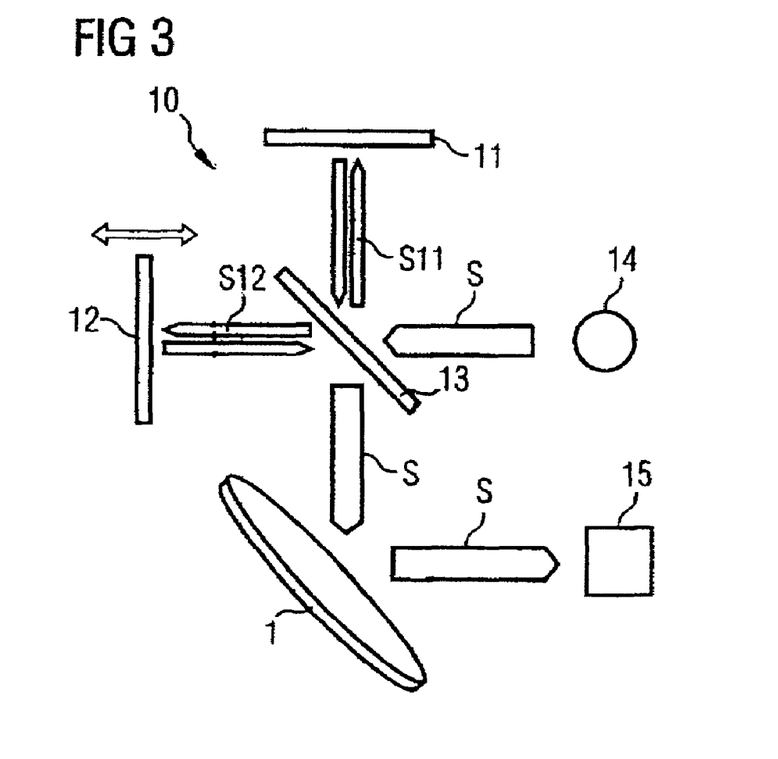
FIG. 3 shows a measuring arrangement with a Michelson interferometer for carrying out the method according to FIG. 1.

FIG. 3 shows a measuring arrangement for carrying out the method according to FIG. 1. The measuring arrangement comprises a radiation source 14, which emits electromagnetic radiation S in the infrared range, a Michelson interferometer 10 for modulating the wavelengths of the radiation S, and a detector 15 for recording the intensity of the radiation S reflected at the semiconductor wafer 1. The Michelson interferometer 10 has a semitransmissive beam splitter 13, a fixed mirror 11 and also a movable mirror 12.

The radiation emerging from the radiation source 14, illustrated by the beam S, is split into two partial beams S11, S12, ideally having the same intensity, at the semitransmissive beam splitter 13. One partial beam S11 is reflected to the stationary mirror 11 and the other partial beam S12 is transmitted through to the movable mirror 12. The two partial beams S11, S12 are reflected at the respective mirror 11, 12 and are superposed again to form a beam S, which then impinges on the semiconductor wafer 1, is reflected there and finally passes to the detector 15.

The detector 15 measures the intensity of the beam S reflected at the semiconductor wafer 1 depending on the position of the movable mirror 12. This intensity profile depending on the position of the movable mirror 12 is also referred to as an interferogram. Computational Fourier transformation of the interferogram yields an intensity spectrum depending on the wave number of the electromagnetic radiation that is radiated in.

The measuring arrangement illustrated in FIG. 3 essentially corresponds to a Fourier transform spectrometer that is customary for spectroscopic examinations. Such a spectrometer is distinguished inter alia by a high intensity of the radiation which is incident on a sample and reflected from the latter, since no dispersive elements or slit-type diaphragms are used. Furthermore, a short measurement time is made possible since the wavelengths are measured simultaneously. In principle, however, other spectrometers, such as, for instance, multibeam spectrometers or grating spectrometers, may also be used for determining an intensity spectrum. Moreover, it is possible to carry out the wavelength modulation with the aid of a laser that can be continuously tuned in the wavelength range and thus to measure an intensity profile depending on the laser wavelength set without recording an interferogram.

As explained above, the intensity spectrum determined depending on the wave number of the electromagnetic radiation that is radiated in contains information about interferences of radiation reflected at the surface of the semiconductor wafer and at the layers brought about by the buried structure. The way in which constructive and destructive interferences can form and the way in which they influence the form of the intensity spectrum 8 become clear from FIG. 4, which shows a diagrammatic intensity spectrum 8 recorded in reflection as a function of the wave number $\upsilon$ of the electromagnetic radiation that is radiated in, and a further diagrammatic sectional illustration of the top side of the semiconductor wafer 1.

Figure 4:
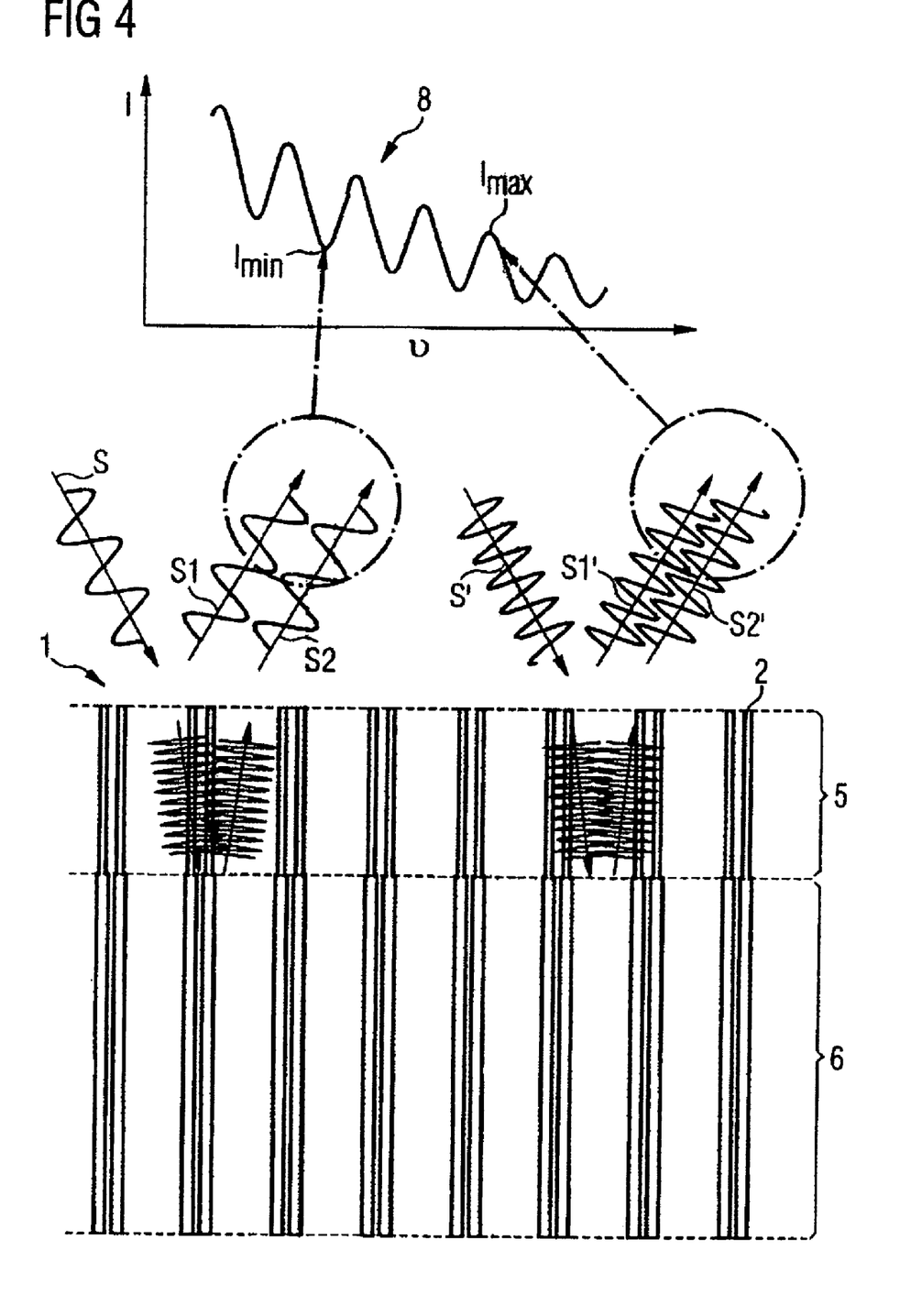
FIG. 4 shows a diagrammatic interference spectrum and a further diagrammatic sectional illustration of the top side of the semiconductor wafer with interfering partial beams having a different wavelength.

In the case of the beam S illustrated on the left-hand side, which represents electromagnetic radiation having a comparatively long wavelength or small wave number $\upsilon$, the optical path difference between the partial beam S1 reflected at the surface of the semiconductor wafer 1 and the partial beam S2 reflected at the interface between upper layer 5 and lower layer 6 brings about a phase shift of a half-integer multiple of the wavelength, so that the two partial beams S1, S2 interfere destructively. In the intensity spectrum 8, an intensity minimum $I_{min}$ can be observed at this wavelength or wave number $\upsilon$.

In contrast to this, the optical path difference in the case of the beam S' illustrated on the right-hand side, with radiation having a comparatively short wavelength or large wave number $\upsilon$, leads to a phase shift between the partial beam S1' reflected at the surface of the semiconductor wafer 1 and the partial beam S2' reflected at the interface between upper layer 5 and lower layer 6 of an integer multiple of the wavelength. The two partial beams S1' and S2' thus interfere constructively, so that the intensity I has an intensity maximum $I_{max}$ at this wavelength or wave number $\upsilon$.

The form of the intensity spectrum 8 can thus be used to deduce the optical path differences at the respective wavelengths and thus the thickness of the upper layer 5 or the depth of the upper trench section. A depth spectrum of the semiconductor wafer 1 can thus be produced with the aid of a frequency analysis of an intensity spectrum.

Figure 5:
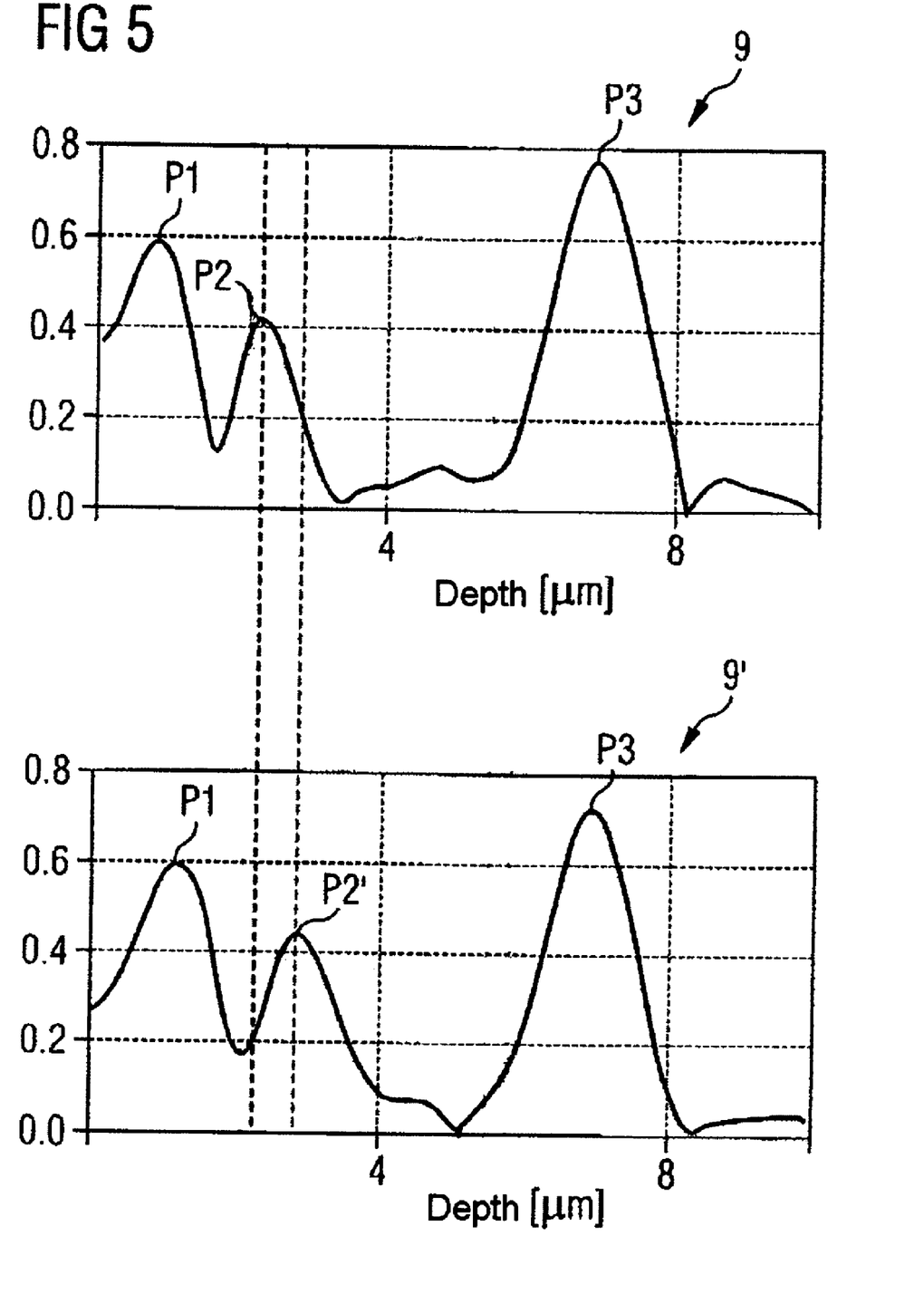
FIG. 5 shows two different depth spectra of the top side of a semiconductor wafer provided with trench structures.

For illustration purposes, FIG. 5 shows two different depth spectra 9, 9' of the top side of a semiconductor wafer provided with trench structures, which were obtained by frequency analysis of intensity spectra. The intensity spectra were recorded after different etching times of the lower trench sections.

Three peaks P1, P2, P3 are clearly discernible in the upper depth spectrum 9 illustrated in FIG. 5. Three peaks P1, P2, P3 can be assigned to interfaces between two layers in each case, at which there is a gradient in the refractive index and reflection thus takes place. The first peak P1 at about 1 µm can be identified as the depth of an upper oxide layer. The second peak P2 stems from reflections at the interface between the upper and lower layers of the trench structure defined by the upper and lower trench sections, respectively, and lies at a depth of approximately 2 µm. This value thus corresponds to the depth of the upper trench section. Finally, another peak P3 can be observed at approximately 7 µm, which stems from reflections at the underside of the lower trench section. This is because reflections occur at this location, too, since the material composition changes, with the result that there is an interface between two layers and thus a gradient in the refractive index.

In contrast to this, in the case of the lower depth spectrum 9', on account of the second peak P2' shifted toward the right, the depth of the upper trench section can be assigned a higher value of approximately 2.6 µm.

In the case of the method explained with reference to the preceding FIGS. 1 to 5, there is the problem that the determination of small depths can become inaccurate. This is the case when the wavelengths of the radiation used are greater than the depth of the buried structure or the size of the optical path differences. This is because constructive or destructive interferences of electromagnetic radiation reflected at the surface of the semiconductor wafer and at the layers brought about by the structure do not occur in such a case, so that the frequency analysis of an intensity spectrum determined may be beset with inaccuracies. In order to avoid these inaccuracies, therefore, another embodiment of a method according to the invention is proposed, which additionally takes account of the change in the state of polarization of the electromagnetic radiation reflected at the semiconductor wafer.

Figure 6:
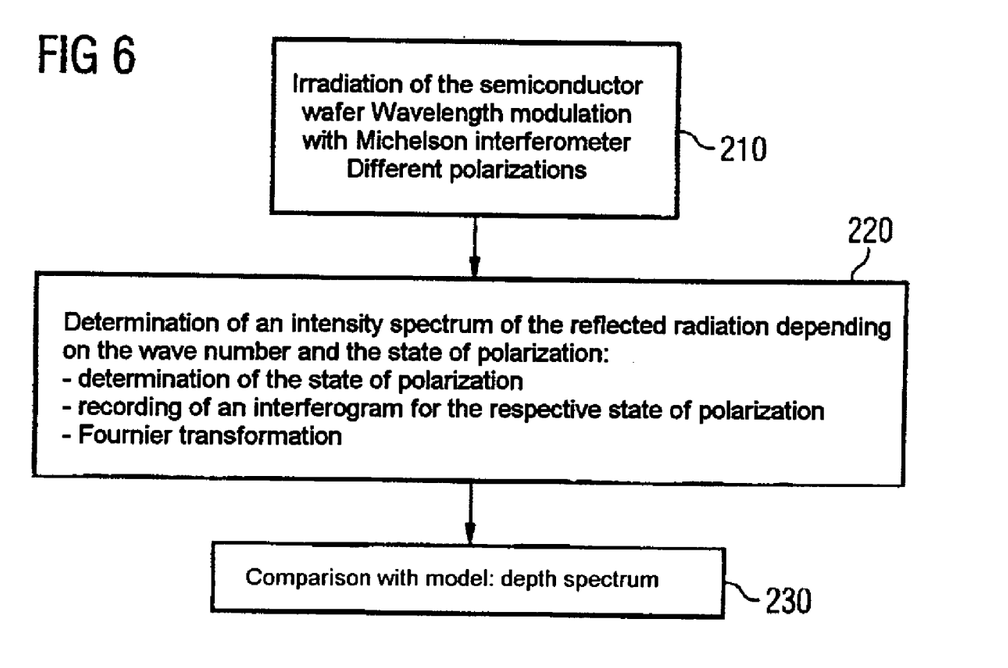
FIG. 6 shows a flow diagram of a second embodiment of a method according to the invention.

FIG. 6 shows a flow diagram of a second embodiment of a method according to the invention. In this case, in 210, the semiconductor wafer is irradiated at a predetermined angle of incidence with respect to a surface of the semiconductor wafer with electromagnetic radiation in the infrared range, the wavelengths again being modulated in a frequency-dependent manner with the aid of a Michelson interferometer. The radiation is additionally oriented in different polarization directions or states of polarization.

Step 220 involves determining an intensity spectrum of the radiation reflected at the surface of the semiconductor wafer depending on the wave number and the state of polarization, which is altered by the reflection. Step 220 can be subdivided into three substeps. A first substep involves determining the state of polarization of the reflected radiation. A second substep involves recording an interferogram for the respective state of polarization and a third substep involves converting this interferogram into an intensity spectrum with the aid of a Fourier transformation.

By comparing the intensity spectra determined in the case of the respective states of polarization with intensity spectra calculated on the basis of a model, a depth spectrum is determined in a third method step 230. This model is based on Fresnel's equations, which incorporate optical parameters of the semiconductor wafer with the buried structure, acting as a layer system, and thus also parameters describing the depth(s) of the buried structure. By varying these parameters, the intensity spectra calculated with the aid of the model are adapted to the measured spectra in order to create a depth spectrum of the buried structure.

Figure 7:
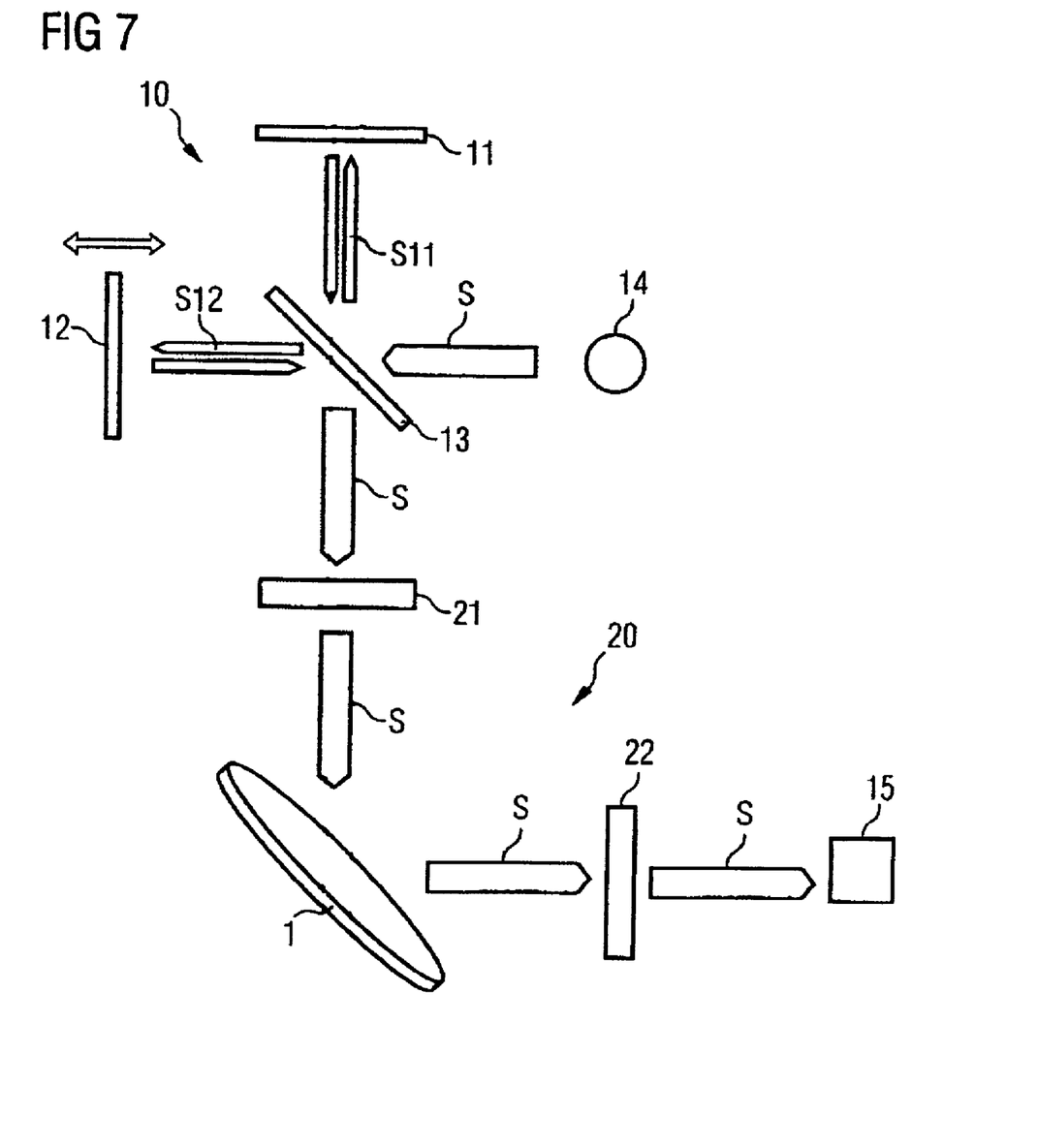
FIG. 7 shows a measuring arrangement with a Michelson interferometer and an ellipsometer for carrying out the method according to FIG. 6.

A measuring arrangement for carrying out this method is illustrated in FIG. 7. The measuring arrangement comprises a radiation source 14, which emits electromagnetic radiation S in the infrared range, and the Michelson interferometer 10 already shown in FIG. 3, with the aid of which the radiation S emitted by the radiation source 14 undergoes a wavelength modulation. After passing through the Michelson interferometer 10, the radiation S impinges on a polarizer 21, which orients the radiation S in a defined state of polarization. After subsequent reflection of the radiation S at the semiconductor wafer 1, the radiation passes through an analyzer 22 and finally passes to a detector 15. The analyzer 22, which, like the polarizer 21, transmits only preferred states of polarization of the electromagnetic radiation S, is used to determine the state of polarization of the radiation S after reflection at the semiconductor wafer 1. This is done for example by rotating the analyzer 22 into different states of polarization until a radiation maximum or minimum occurs in the detector 15.

After the state of polarization of the reflected radiation S has been determined, the detector 15 records an interferogram, which can be used to calculate an intensity spectrum depending on the wave number by means of Fourier transformation.

The measuring arrangement illustrated in FIG. 7 essentially comprises the coupling of a Fourier transform spectrometer to an ellipsometer 20, the ellipsometer 20 with the polarizer 21 and the analyzer 22 being used for determining the change in the state of polarization of the radiation S reflected at the semiconductor wafer 1. Instead of the ellipsometer 20 illustrated, it is also possible to use other types of ellipsometer which also have additional optical elements.

Figure 8:
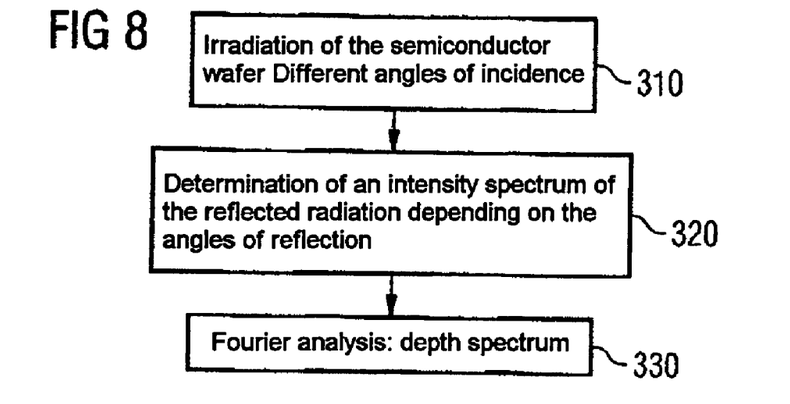
FIG. 8 shows a flow diagram of a third embodiment of a method according to the invention.

The determination of the depth of a buried structure in a semiconductor wafer can also be effected by means of an angle-dependent intensity spectrum with respect to a predetermined wavelength, instead of a wave-number-dependent intensity spectrum. In this respect, FIG. 8 shows a flow diagram of a third embodiment of a method according to the invention.

In this case, in 310, the semiconductor wafer is irradiated at different angles of incidence or a continuously tuned range of angles of incidence with respect to a surface of the semiconductor wafer with electromagnetic radiation having a predetermined wavelength lying in the infrared range, and in 320 involves recording an intensity spectrum of the radiation reflected at the semiconductor wafer at angles of reflection corresponding to the angles of incidence with respect to the surface of the semiconductor wafer.

An intensity spectrum determined in this way depending on the angles of reflection includes information about constructive and destructive interferences of radiation of one wavelength which is reflected at the surface of the semiconductor wafer and at the layers brought about by the buried structure, and thus about different optical path differences depending on the angles of incidence and reflection.

With the aid of an angle of reflection specific Fourier analysis of such an intensity spectrum, it is therefore possible, in 330, to determine the depth of reflections at the buried structure and thus a depth spectrum.

Figure 9:
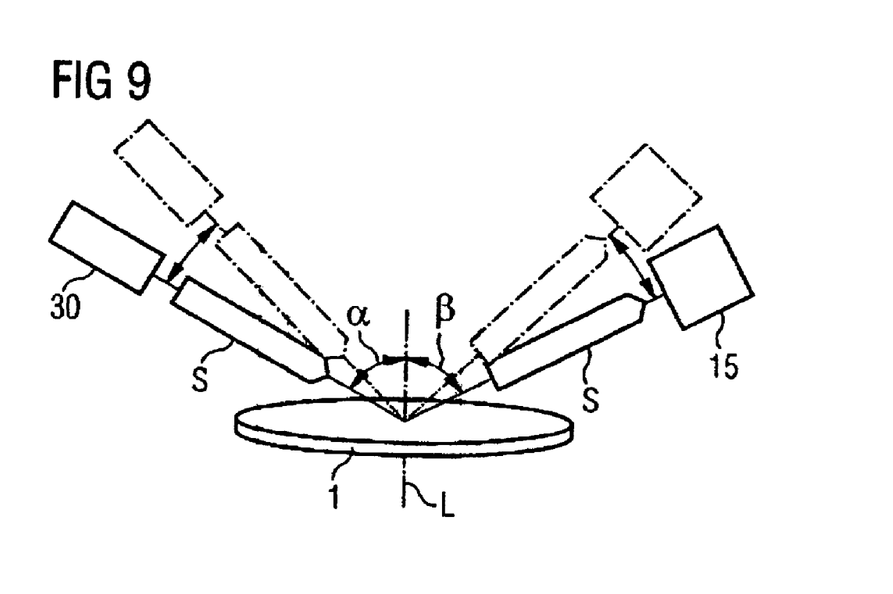
FIG. 9 shows a measuring arrangement for carrying out the method according to FIG. 8.

This method can be carried out in accordance with the measuring arrangement illustrated in FIG. 9. The radiation source used is a laser 30, which emits coherent electromagnetic radiation S of high intensity. The semiconductor wafer 1 is irradiated at different angles a of incidence or a continuously tuned range of angles of incidence with respect to the surface of the semiconductor wafer 1 with radiation S from the laser 30 and a detector 15 subsequently records the intensity of the radiation S reflected at the semiconductor wafer 1 at the angles β of reflection corresponding to the angles α of incidence. In this case, the use of the laser 30 promotes a highly accurate recording of the intensity spectrum.

As an alternative, this method also affords the possibility of comparing a measured intensity profile with an intensity profile calculated on the basis of a model, in order to determine the depth of the buried structure. In accordance with the second embodiment of a method according to the invention as described above, it is favorable in this case to take account of the change in the state of polarization upon the reflection of the electromagnetic radiation at the semiconductor wafer in the model. The change in the state of polarization may again be determined with the aid of an ellipsometer.

Figure 10:
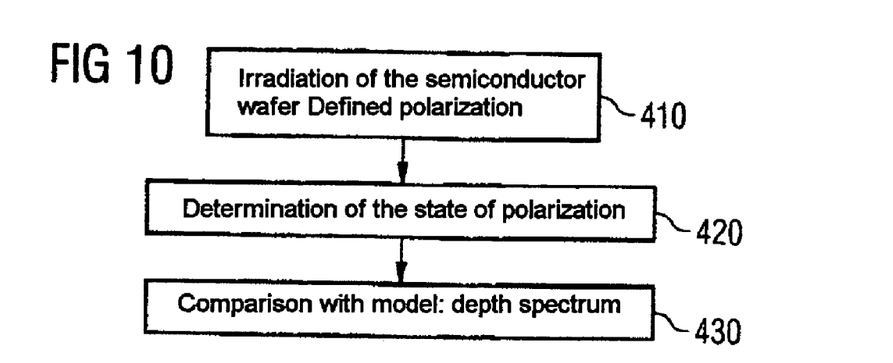
FIG. 10 shows a flow diagram of a fourth embodiment of a method according to the invention.

It is furthermore possible to determine the depth of a buried structure in a semiconductor wafer merely by means of ellipsometric methods. In this respect, FIG. 10 shows a flow diagram of a fourth embodiment of a method according to the invention for determining the depth of a buried structure in a semiconductor wafer.

In this method, in 410, the semiconductor wafer is irradiated at a predetermined angle of incidence with respect to a surface of the semiconductor wafer with electromagnetic radiation having a defined polarization, the electromagnetic radiation having a wavelength in the infrared range. Afterward, 420 involves determining the state of polarization that has been changed by the reflection of the radiation at the semiconductor wafer at an angle of reflection corresponding to the angle of incidence with respect to the surface of the semiconductor wafer. In 430, the state of polarization determined is compared with a change in the state of polarization calculated on the basis of a model which takes account of the depth(s) of the buried structure, in order to obtain a depth spectrum of the semiconductor wafer.

Figure 11:
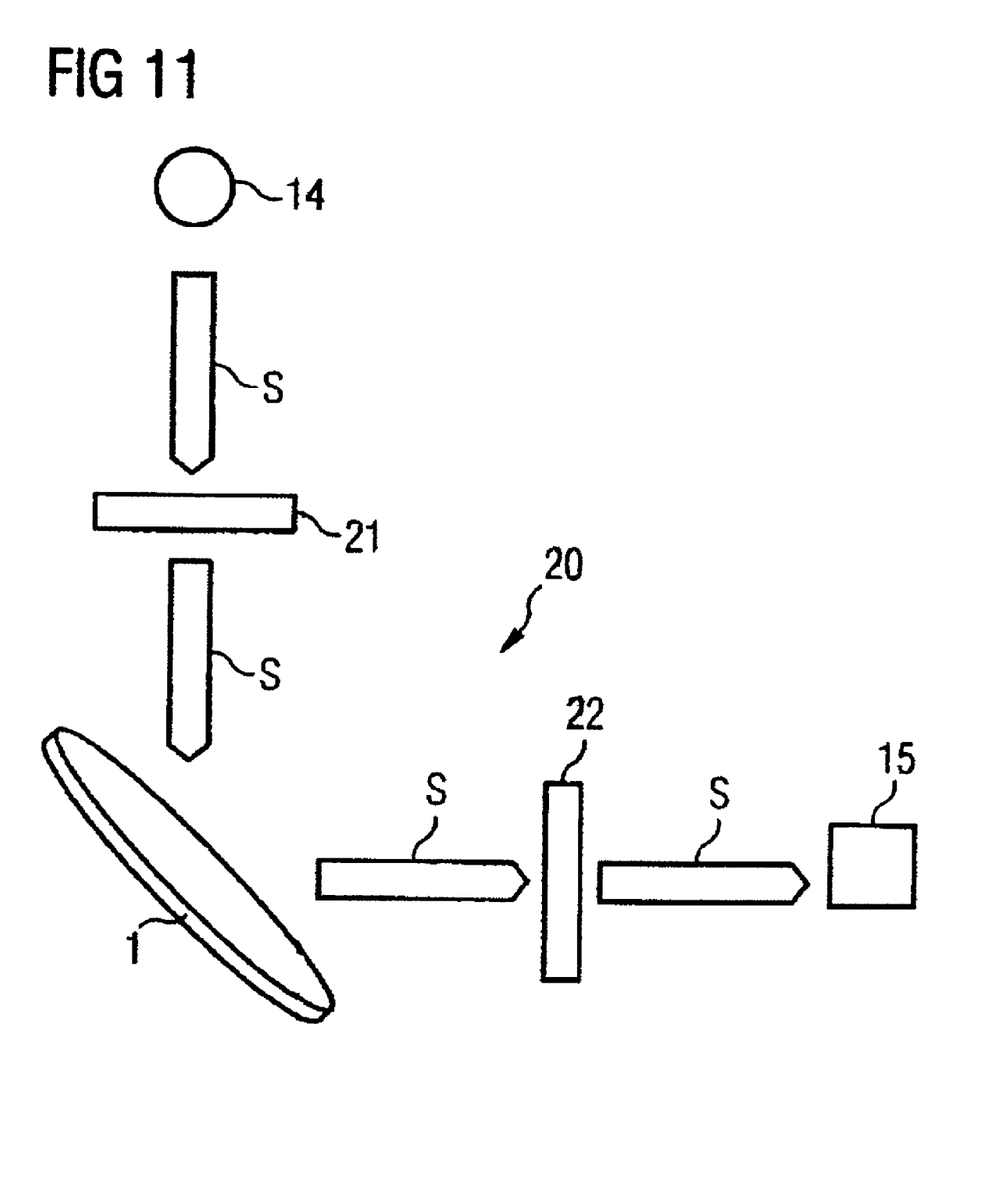
FIG. 11 shows a measuring arrangement with an ellipsometer for carrying out the method according to FIG. 10.

This method can be carried out with the aid of the ellipsometer 20 illustrated in FIG. 11. In this case, the electromagnetic radiation S emitted by a radiation source 14 is oriented in a specific state of polarization in a polarizer 21. After reflection at the semiconductor wafer 1, the radiation S passes through an analyzer 22 before impinging on a detector 15. The state of polarization of the reflected radiation S can again be determined with the aid of the analyzer 22 and the detector 15. This purely ellipsometric measurement method can be carried out both at one wavelength and in a wavelength range. It is also possible to use different types of ellipsometer depending on the measurement method chosen. If a method at one wavelength is preferred, a suitable radiation source is once again a laser, in order to be able to effect measurement by means of coherent electromagnetic radiation of high intensity.

Instead of the previously described embodiments according to the invention for determining the depth of a buried structure in a semiconductor wafer, alternative embodiments which represent further combinations of spectrometric and/or ellipsometric methods are conceivable. It is possible, for example, to record intensity profiles in a wavelength range at different angles of incidence and reflection and, if appropriate, additionally to take account of the change in the polarization of the radiation when determining a depth spectrum.

Moreover, it is obvious to the person skilled in the art that the methods are also suitable for determining the depth of structures extending geometrically within the semiconductor wafer, hidden structures or else desired inclusion volumes, as are represented by microelectromechanical systems, for example. This naturally presupposes that these structures bring about a material change associated with a gradient in the refractive index in the semiconductor wafer, so that reflections take place at the structures.

| List of reference symbols | |
|---|---|
| 1 | Semiconductor wafer |
| 2 | Trench structure |
| 3 | Upper trench section |
| 4 | Lower trench section |
| 5 | Upper layer |
| 6 | Lower layer |
| 7 | Path difference |
| 8 | Intensity spectrum |
| 9 | Depth spectrum |
| 10 | Michelson interferometer |
| 11 | Fixed mirror |
| 12 | Movable mirror |
| 13 | Beam splitter |
| 14 | Radiation source |
| 15 | Detector |
| 20 | Ellipsometer |
| 21 | Polarizer |
| 22 | Analyzer |
| 30 | Laser |
| 110, 120, 130 | Method step |
| 210, 220, 230 | Method step |
| 310, 320, 330 | Method step |
| 410, 420, 440 | Method step |
| A | Point |
| I | Intensity |
| $I_{max}$ | Maximum |
| $I_{min}$ | Minimum |
| L | Perpendicular |
| S | Radiation/beam |
| S1, S2 | Partial beam |
| S11, S12 | Partial beam |
| P1, P2, P3 | Peak |
| α | Angle of incidence |
| β | Angle of reflection |
| γ | Angle of refraction |
| υ | Wave number |

What is claimed is:

1. A method for determining a thickness of a structured layer in a semiconductor wafer, wherein the structured layer has structure elements arranged in a regular pattern, comprising:
   irradiating the semiconductor wafer over a large area at a predetermined angle of incidence with respect to a surface of the semiconductor wafer with electromagnetic radiation extending over a wavelength range, wherein the irradiated area comprises a plurality of the structure elements of the structured layer, and the wavelengths of the electromagnetic radiation are substantially greater than lateral dimensions of the structure elements of the structured layer so that the electromagnetic radiation suppresses scattering effects at the structure elements and, thereby, the structured layer appears homogeneous to the electromagnetic radiation with regard to optical properties;
   recording the intensity of the reflected radiation depending on a wave number of the wavelength range of the radiated-in electromagnetic radiation at an angle of reflection, corresponding to the angle of incidence, with respect to the surface of the semiconductor wafer; and
   determining the thickness of the structured layer from the recorded intensity depending on the wave numbers.

2. The method as claimed in claim 1, wherein the thickness of the structured layer is determined by a frequency analysis of the intensity.

3. The method as claimed in claim 1, wherein the thickness of the structured layer is determined by comparing the measured intensity profile with an intensity profile calculated based on a model.

4. The method as claimed in claim 3, wherein the semiconductor wafer is irradiated with electromagnetic radiation with different polarizations, and, to determine the thickness of the structured layer, a respective state of polarization of the measured intensity is additionally taken into account in the model.

5. The method as claimed in claim 1, wherein a wavelength modulation is used for irradiating the semiconductor wafer, the wavelength modulation effected with aid of a movable mirror of a Michelson interferometer, and the recording comprising:
   recording the intensity of the reflected radiation depending on a position of the movable mirror; and
   calculating the intensity of the reflected radiation depending on the wave number by Fourier transformation of the intensity recorded depending on the position of the movable mirror.

6. The method as claimed in claim 1, wherein a wavelength modulation is used for irradiating the semiconductor wafer, the wavelength modulation effected with aid of a laser that is continuously tuned in the wavelength range.

7. The method as claimed in claim 1, wherein the wavelengths of the electromagnetic radiation lie in the range of 2 to 20 μm, and the lateral dimensions of the structure elements lie in the region of 100 nm.

8. The method as claimed in claim 1, wherein the structure elements of the structured layer comprise trench columns.

9. The method as claimed in claim 1, further comprising determining a depth of an upper trench column of a trench structure for a trench capacitor, wherein the trench structure comprises the upper trench column and a wider lower trench column.

10. The method as claimed in claim 1, wherein the electromagnetic radiation lies in an infrared range.

11. The method as claimed in claim 1, wherein the reflected radiation includes radiation reflected from a top surface of the structured layer and radiation reflected from a bottom surface of the structured layer.

12. The method as claimed in claim 1, wherein the structured layer is positioned on top of a second layer.

13. The method as claimed in claim 12, wherein the structured layer possesses a first set of optical properties and the second layer possesses a second set of optical properties that is different from the first set of optical properties.

14. The method as claimed in claim 12, wherein the second layer comprises a plurality of second structure elements arranged in a regular pattern and the wavelengths of the electromagnetic radiation are substantially greater than lateral dimensions of the second structure elements, so that the electromagnetic radiation suppresses scattering effects at the second structure elements of the second structured layer and, thereby, the second layer appears homogeneous to the electromagnetic radiation.

15. The method as claimed in claim 14, wherein the structured layer possesses a first set of optical properties and the second layer possesses a second set of optical properties that is different from the first set of optical properties.

* * * * *